(12) United States Patent
Yokota et al.

(10) Patent No.: US 7,614,423 B2
(45) Date of Patent: Nov. 10, 2009

(54) CONNECTOR

(75) Inventors: Takayuki Yokota, Nakakoma-gun (JP);
Yoshinori Hishikawa, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 217 days.

(21) Appl. No.: 10/577,662

(22) PCT Filed: Nov. 2, 2004

(86) PCT No.: PCT/JP2004/016270

§ 371 (c)(1),
(2), (4) Date: May 1, 2006

(87) PCT Pub. No.: WO2005/042070

PCT Pub. Date: May 12, 2005

(65) Prior Publication Data

US 2007/0028979 A1    Feb. 8, 2007

(30) Foreign Application Priority Data

Nov. 4, 2003   (JP)   ............... 2003-374034

(51) Int. Cl.
*F16K 11/02* (2006.01)
*F16L 29/04* (2006.01)

(52) U.S. Cl. ............ 137/606; 251/149.6; 604/167.04

(58) Field of Classification Search ............ 137/602, 137/605, 606, 861, 877, 878, 881; 251/149, 251/149.1, 149.4, 149.6; 604/167.04, 244, 604/246

See application file for complete search history.

(56) References Cited

U.S. PATENT DOCUMENTS 4,449,693 A * 5/1984 Gereg .................. 251/149.8
5,201,725 A   4/1993 Kling (Continued)

FOREIGN PATENT DOCUMENTS

JP        5-32071        5/1993

(Continued)

OTHER PUBLICATIONS

U.S. Appl. No. 10/557,832, filed May 1, 2006, Takayuki Yokota et al.

*Primary Examiner*—Stephen Hepperle
*Assistant Examiner*—William McCalister
(74) *Attorney, Agent, or Firm*—Buchanan Ingersoll & Rooney PC (57) ABSTRACT

A connector having a male-side connection section, a liquid flow section where a liquid flow space communicating with the inside of the male-side connection section is provided, a first female-side connection opening and a second female-side connection opening, and a first valve body and a second valve body that are made from an elastic material. The first valve body has a head section and a neck section that connects the head section and a liquid flow section and is thinner than the head section. In the first valve body is formed a slit penetrating from the top face of the head section to the liquid flow space. When a male lure is connected to the first female-side connection opening, the slit is opened and the flow path in the male lure and the inside of the male-side connection section are communicated through the liquid flow space.

10 Claims, 12 Drawing Sheets

U.S. PATENT DOCUMENTS

| | | | | |
|---|---|---|---|---|
| 5,273,533 | A | * | 12/1993 | Bonaldo ................. 604/83 |
| 5,501,426 | A | * | 3/1996 | Atkinson et al. ......... 251/149.1 |
| 5,509,912 | A | | 4/1996 | Vaillancourt et al. |
| 5,676,346 | A | * | 10/1997 | Leinsing ................. 251/149.1 |
| 2002/0017127 | A1 | | 2/2002 | Nakano et al. |
| 2003/0036735 | A1 | | 2/2003 | Jepson et al. |
| 2007/0218745 | A1 | | 9/2007 | Yokota et al. |

FOREIGN PATENT DOCUMENTS

| | | |
|---|---|---|
| JP | 09-108361 | 4/1997 |
| JP | 3052138 | 9/1998 |
| JP | 2002-035140 | 2/2002 |
| JP | 2003-144546 | 5/2003 |
| WO | WO 89/06553 | 7/1989 |

* cited by examiner

CONNECTOR

TECHNICAL FIELD

The present invention relates to a connector having a valve mechanism for opening and closing a flow passage when a tube is connected and disconnected.

BACKGROUND ART

Medical circuits for use in fluid infusion, blood infusion, parenteral nutrition administration, etc. are occasionally connected and disconnected for continuously or temporarily supplying fluids such as a plurality of medicinal solutions, blood, liquid diet, etc. It is well known in the art that connectors are incorporated into those medical circuits for connection and disconnection (see, for example, Japanese Laid-Open Patent Publication No. 9-108361 and Japanese Patent Publication No. 5-32071).

A typical one of the connectors is a three-way cock. The three-way cock comprises a single male lure connector and two female lure connectors which are fitted to each other to connect the circuit. However, the three-way cock is disadvantageous in that it is vulnerable to bacterial contamination because a fluid passage region thereof is exposed to external air when the circuit is disconnected. Particularly, the female joint is frequently brought into contact with external air because it is used many times for repeated connection and disconnection.

There is known a connector having a valve body in a female joint port for preventing a fluid passage region thereof from being exposed to external air. According to the connector, the valve body is pierced by a needle or a male connector is inserted into the valve body that has a slit, opening the fluid passage. After the needle or the male connector is removed, the valve body is closed again, preventing the fluid passage from being exposed to external air.

However, the above connectors are problematic in that since the valve body is mounted in only one female joint port, when the male connector is removed from the other female joint port, the female joint port is exposed to the atmospheric air.

The above connectors are also disadvantageous in that the female joint ports tend to trap a fluid, making it difficult for a medical solution to flow in its entirety so that an environment for easy bacterial growth tends to be created. Furthermore, though the connector needs to be filled with a fluid such as a medical solution or the like before it is used, existing air in the connector cannot easily be removed.

Further, when a needle or a male connector is attached to and removed from a female joint port, the contents of the connector are liable to change. For example, if the contents of the connector increase when the male connector is removed, the blood flows from a blood vessel catheter connected to the connector back into the blood vessel catheter, causing the blood vessel catheter to be closed off.

DISCLOSURE OF THE INVENTION

It is an object of the present invention to provide a connector which is capable of preventing a flow passage from being contaminated by reliably opening and closing the flow passage, as a tube is connected and disconnected, and which makes a fluid less liable to be trapped therein.

To achieve the above object, a connector according to the present invention comprises:
a tubular male joint member;
a liquid passage portion having a liquid passage space defined therein in fluid communication with an interior of the male joint member;
a first female joint port and a second female joint port each of which is capable of receiving a tube;
a first valve body having a head and a neck interconnecting the head and the liquid passage portion, the neck being thinner than the head, the first valve body having a slit extending from a top surface of the head to the liquid passage space, the first valve body being made of an elastic material; and
a second valve body having a head and a neck interconnecting the head and the liquid passage portion, the neck being thinner than the head, the second valve body having a slit extending from a top surface of the head to the liquid passage space, the second valve body being made of an elastic material;
wherein when a tube is connected to the first female joint port, the first valve body is deformed to open the slit of the first valve body to bring an interior of the tube and an interior of the male joint member into fluid communication with each other through the slit of the first valve body and the liquid passage space; and
when a tube is connected to the second female joint port, the second valve body is deformed to open the slit of the second valve body to bring an interior of the tube and the interior of the male joint member into fluid communication with each other through the slit of the second valve body and the liquid passage space.

With the above arrangement, since the flow passage is reliably opened and closed when the tube is connected and disconnected, the flow passage is prevented from being contaminated. The connector is also prevented from developing regions therein where the liquid is trapped.

In the connector according to the present invention, the first female joint port or the second female joint port and the male joint member preferably have respective central lines extending substantially parallel to each other.

In the connector according to the present invention, the liquid passage portion, the first valve body, and the second valve body are preferably formed integrally with each other.

In the connector according to the present invention, at least one of the first female joint port and the second female joint port is preferably movable in the direction of a central line thereof relatively to the corresponding valve body.

To achieve the above object, a connector according to the present invention comprises:
a tubular male joint member;
a liquid passage portion having a liquid passage space defined therein in fluid communication with an interior of the male joint member;
a first female joint port and a second female joint port each of which is capable of receiving a tube;
a first valve body disposed in the first female joint port and made of an elastic material, the first valve body having a slit; and
a second valve body disposed in the second female joint port and made of an elastic material, the second valve body having a slit;
the first valve body and the second valve body having respective central lines, which are skew lines;
wherein when a tube is connected to the first female joint port, the first valve body is deformed to open the slit of the first valve body to bring an interior of the tube and an interior of the male joint member into fluid communication with each other through the slit of the first valve body; and
when a tube is connected to the second female joint port, the second valve body is deformed to open the slit of the second valve body to bring an interior of the tube and the interior of the male joint member into fluid communication with each other through the slit of the second valve body.

With the above arrangement, since the flow passage is reliably opened and closed when the tube is connected and disconnected, the flow passage is prevented from being contaminated. The connector is also prevented from developing regions therein where the liquid is trapped.

In the connector according to the present invention, the first female joint port is preferably movable in the direction of the central line thereof relatively to the first valve body, and the second female joint port is preferably movable in the direction of the central line thereof relatively to the second valve body.

To achieve the above object, a connector according to the present invention comprises:

a tubular male joint member;

a liquid passage portion having a liquid passage space defined therein in fluid communication with an interior of the male joint member;

a valve body disposed fixedly with respect to the male joint member and having a head and a neck interconnecting the head and the liquid passage portion, the neck being thinner than the head, the valve body having a slit extending from a top surface of the head to the liquid passage space, the valve body being made of an elastic material; and a housing having a female joint port capable of receiving a tube, the housing being movable in the direction of a central line of the female joint port with respect to the valve body and the male joint member, the housing accommodating the valve body therein;

wherein when a tube is inserted into and connected to the female joint port, the tube presses the valve body to move the valve body and the male joint member with respect to the housing, and to deform the valve body to open the slit, bringing an interior of the tube and an interior of the male joint member into fluid communication with each other through the slit and the liquid passage space.

With the above arrangement, since the flow passage is reliably opened and closed when the tube is connected and disconnected, the flow passage is prevented from being contaminated. The connector is also prevented from developing regions therein where the liquid is trapped.

In the connector according to the present invention, the housing preferably has a tapered portion disposed behind the female joint port and having an inside diameter along the width of the slit, the inside diameter being progressively reduced into the female joint port, and when the tube is connected to the female joint port, the tube presses the valve body to move the valve body into the tapered portion, so that the valve body is pressed and deformed along the width of the slit directly or indirectly by a tapered surface of the tapered portion, thereby opening the slit.

The connector according to the present invention preferably further comprises:

a support member disposed fixedly with respect to the male joint member and supporting the head of the valve body from the neck;

the housing having a tapered portion disposed behind the female joint port and having an inside diameter along the width of the slit, the inside diameter being progressively reduced into the female joint port;

wherein when the tube is connected to the female joint port, the tube presses the valve body to move the valve body together with the support member into the tapered portion, so that the head of the valve body is pressed and deformed along the width of the slit directly by a tapered surface of the tapered portion, and the neck of the valve body is pressed and deformed along the width of the slit by the tapered surface indirectly through the support member, thereby opening the slit.

The connector according to the present invention preferably further comprises:

an urging means for urging the housing to return to an original position when the tube is removed from the female joint port.

In the connector according to the present invention, the fluid passage space is preferably of a shape for preventing a liquid from being trapped therein when the liquid flows in the liquid passage space.

In the connector according to the present invention, the female joint port preferably has an inside diameter along the width of the slit, greater than the inside diameter thereof in a direction perpendicular to the width of the slit.

BEST MODE FOR CARRYING OUT THE INVENTION

A connector according to the present invention will be described in detail below based on a preferred embodiment shown in the accompanying drawings.

Figure 1:
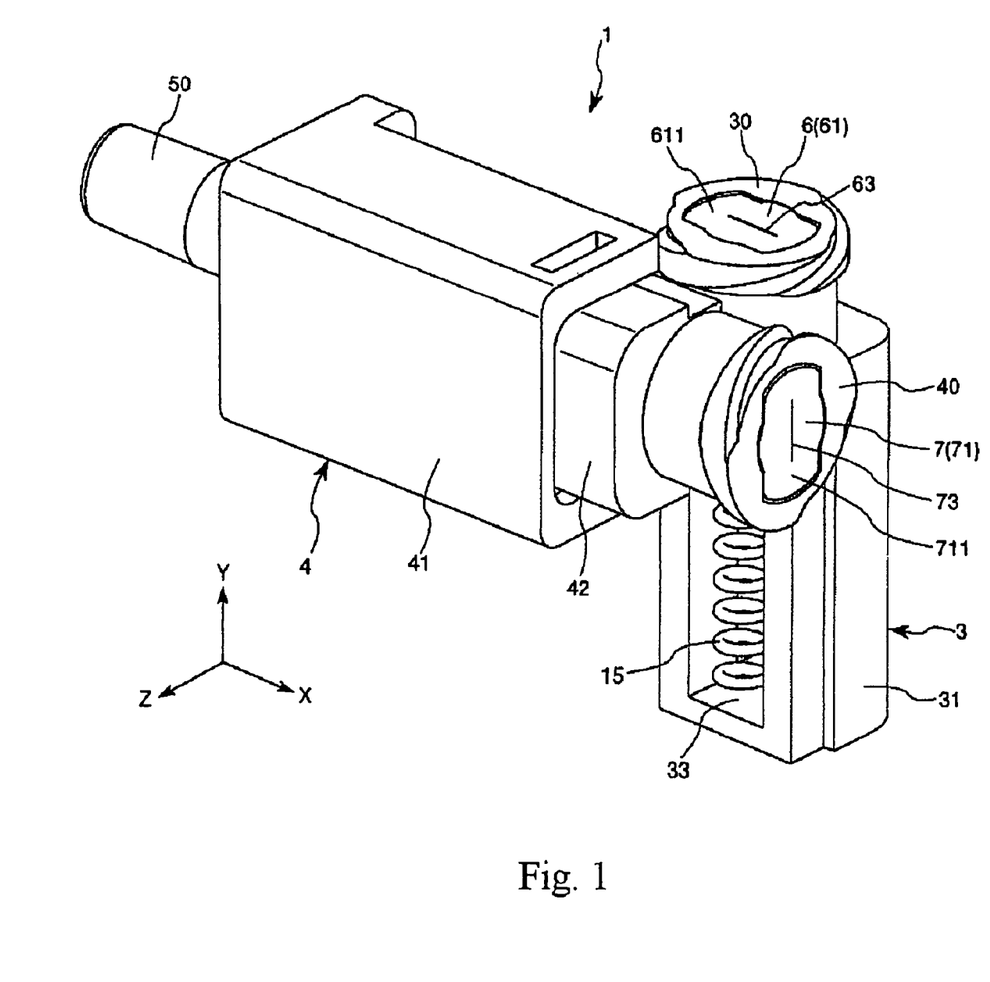
FIG. 1 is a perspective view of a connector according to an embodiment of the present invention.
Figure 2:
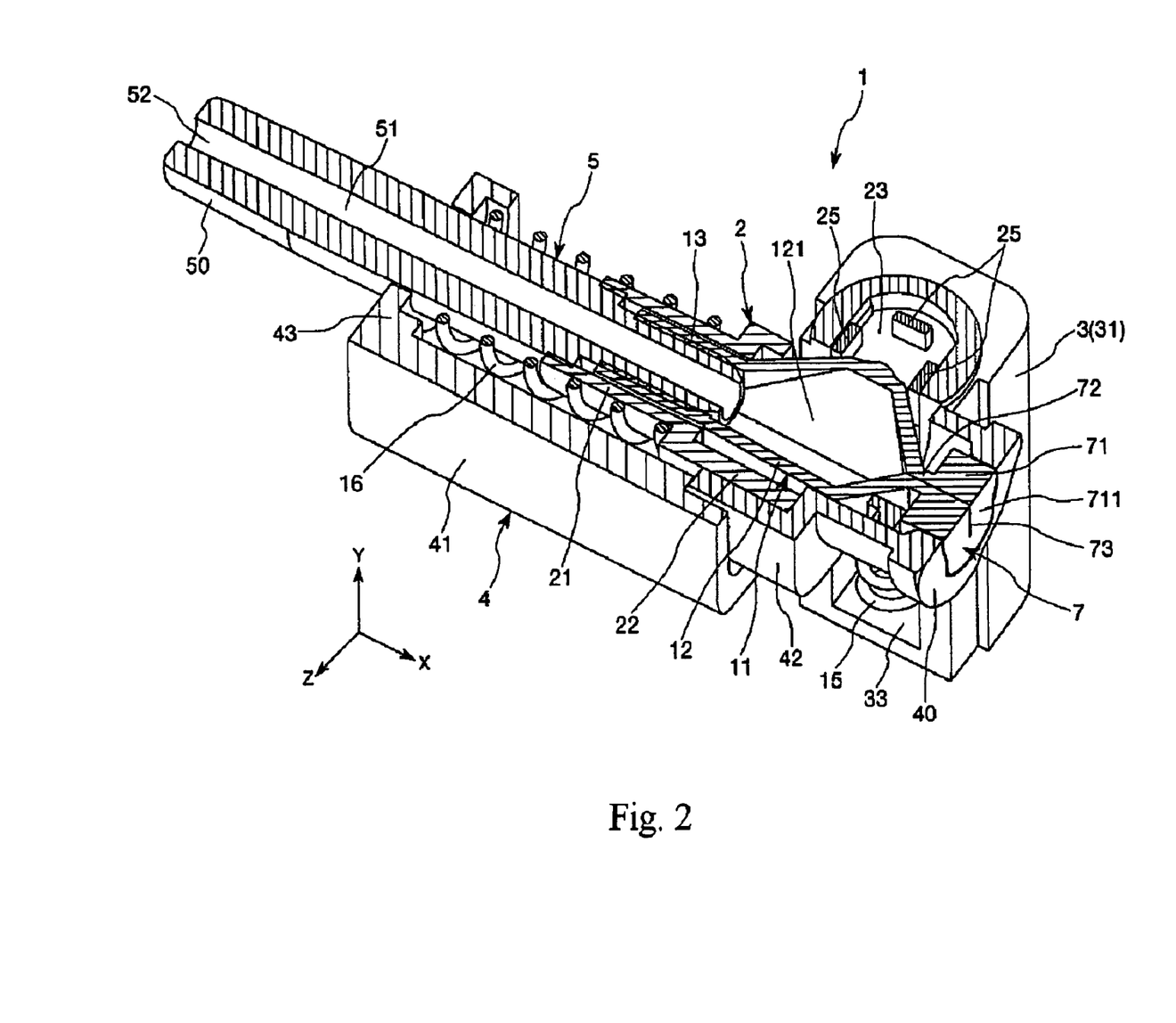
FIG. 2 is a sectional perspective view of the connector shown in FIG. 1.
Figure 3:
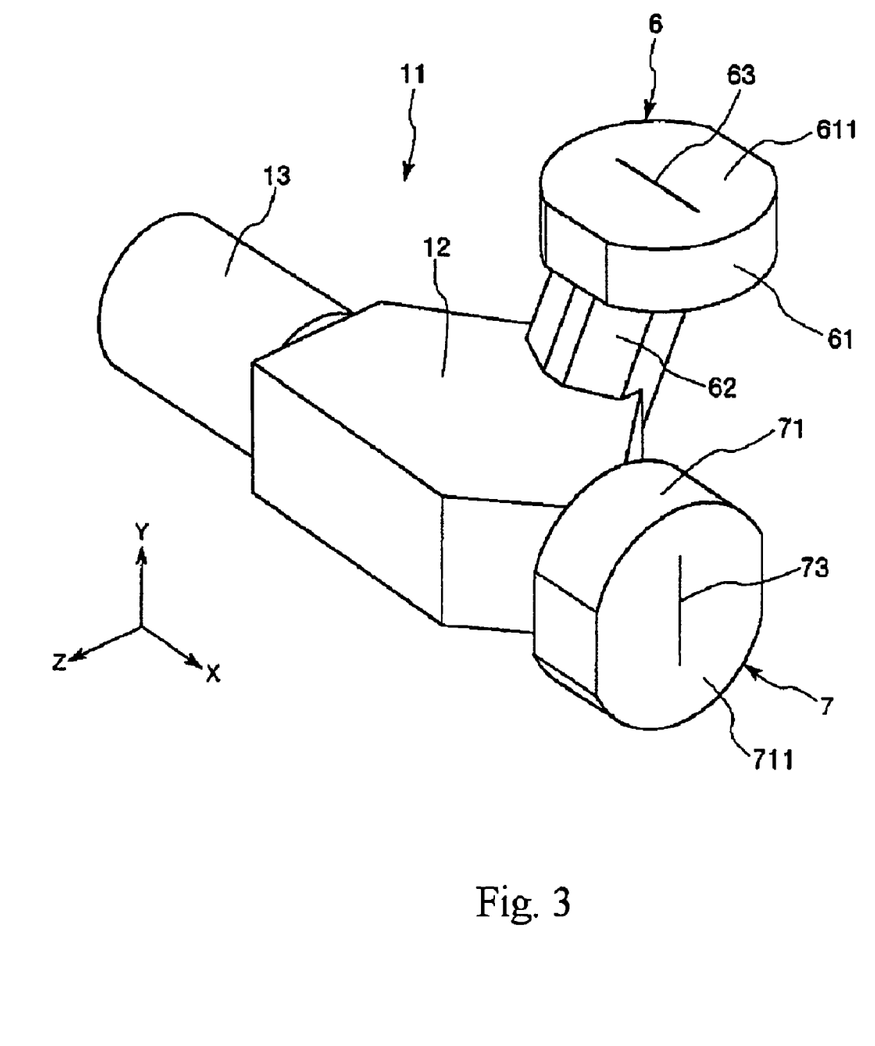
FIG. 3 is a perspective view of a valve assembly incorporated in the connector shown in FIG. 1.
Figure 4:
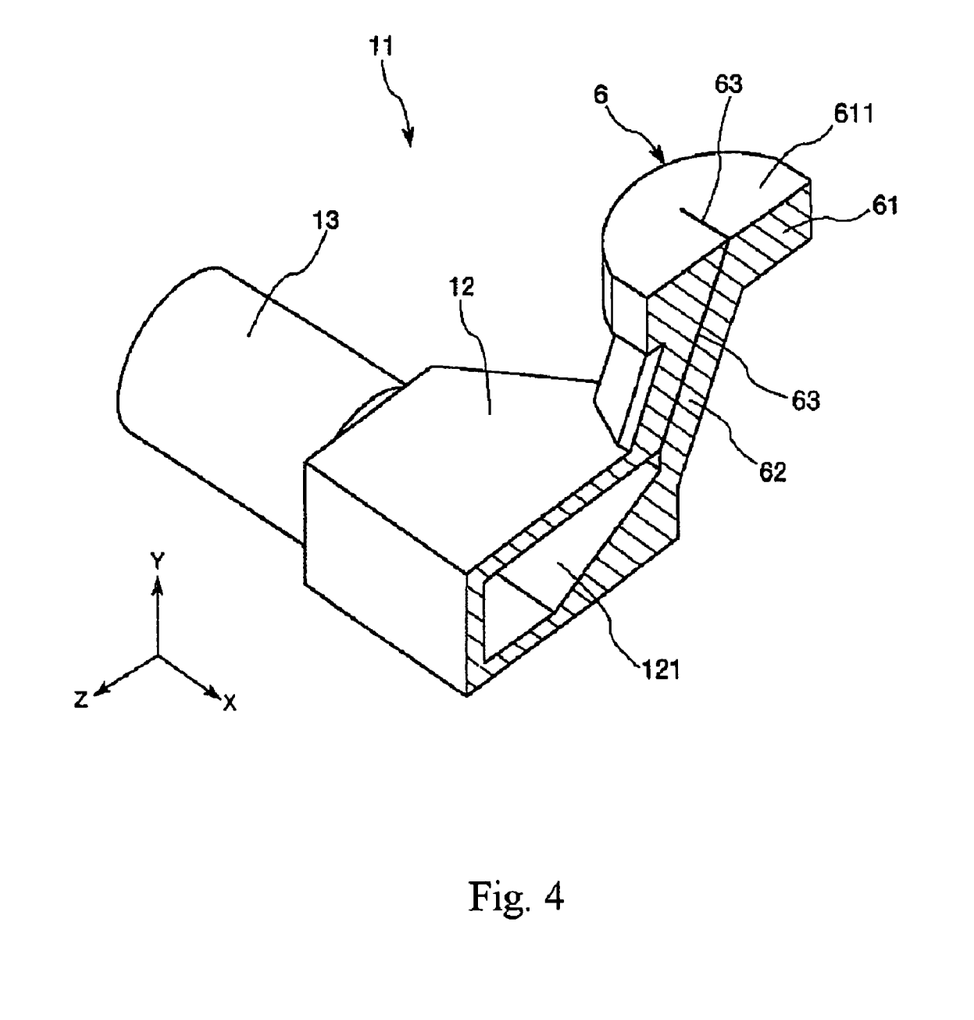
FIG. 4 is a sectional perspective view of the valve assembly incorporated in the connector shown in FIG. 1.
Figure 5:
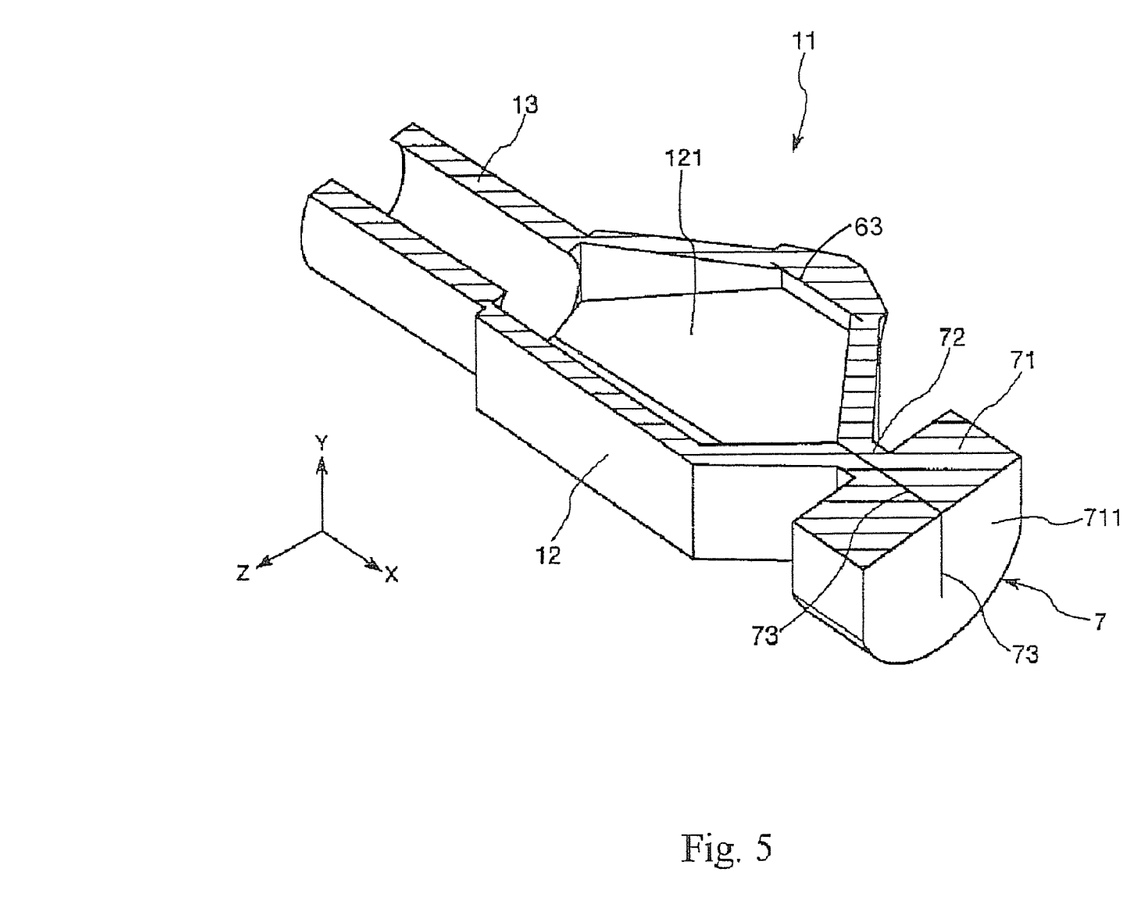
FIG. 5 is a sectional perspective view of the valve assembly incorporated in the connector shown in FIG. 1.

FIG. 1 is a perspective view of a connector according to an embodiment of the present invention, FIG. 2 is a sectional perspective view of the connector shown in FIG. 1, FIG. 3 is a perspective view of a valve assembly incorporated in the connector shown in FIG. 1, FIGS. 4 and 5 are sectional perspective views, respectively of a valve assembly incorporated in the connector shown in FIG. 1, and FIGS. 6 through 12 are sectional perspective views, respectively, of the connector shown in FIG. 1.

A connector 1 shown in these figures is used in combination with a medical instrument which needs to be connected to a fluid flow passage, such as a fluid infusion set (blood infusion set), a parenteral nutrition set, a pressure monitoring line, an artificial lung circuit, an artificial dialysis circuit, etc.

As shown in FIG. 1, the connector 1 has a first female joint port 30 and a second female joint port 40 which are capable of receiving a tube therein, a male joint member 50, a first valve body 6 disposed in the first female joint port 30, and a second valve body 7 disposed in the second female joint port 40.

Tubes which provide flow passages (e.g., a projecting tip end of a syringe, an independent hub or sheath, or the like) can be inserted into and connected to the first female joint port 30 and the second female joint port 40, respectively.

The first female joint port 30 and the second female joint port 40 have respective central lines, which are skew lines and angularly spaced from each other by about 90°. In the description which follows, a direction parallel to the central line of the first female joint port 30 will be referred to as "Y-axis direction", and a direction parallel to the central line of the second female joint port 40, i.e., a direction perpendicular to the Y-axis direction, as "X-axis direction". A direction perpendicular to both the Y-axis direction and the X-axis direction is referred to as "Z-axis direction".

The first female joint port 30 is defined as part of a first housing 3. The first housing 3 has a housing body 31 substantially in the form of a rectangular parallelepiped which is elongate in the Y-axis direction and the first female joint port 30 disposed on one end of the housing body 31. The housing body 31 has a side closer to the viewer of FIG. 1 which is free of a side wall and is open.

The second female joint port 40 is defined as part of a second housing 4. The second housing 4 has a housing body 41 substantially in the form of a rectangular parallelepiped which is elongate in the X-axis direction, a reduced-diameter member 42 slightly thinner than the housing body 41, and the second female joint port 40 disposed on one end of the reduced-diameter member 42. The housing body 41 has a side remoter from the viewer of FIG. 1 which is free of a side wall and is open.

The male joint member 50 comprises a tubular member with a flow passage 51 defined therein and has its central line extending in the X-axis direction. The male joint member 50 has a lure taper whose outside diameter is progressively reduced toward its tip end. The male joint member 50 can be inserted into and connected to a female joint port of another instrument (e.g., an opening in the proximal end of a catheter hub).

As shown in FIG. 2, a tubular member 5 is inserted in the housing body 41. The tubular member 5 has an end portion (remote from the second female joint port 40) serving as the male joint member 50.

A support body 2 is disposed on the other end of the tubular member 5, and supports a valve assembly 11. The tubular member 5 has a flow passage 51 defined therein which has an end communicating with a liquid passage space 121 defined in the valve assembly 11.

A plurality of connectors 1 may be put together and may have their male joint members 50 inserted into and connected to the second female joint ports 40 of the other connectors 1, so that the connectors 1 can be used as an interconnected assembly. Since the second female joint ports 40 and the male joint members 50 are oriented parallel to each other and open away from each other, the connectors 1 can be connected in a linear array and hence can be connected in a form that can easily be used.

As shown in FIG. 3, the valve assembly 11 comprises a first valve body 6, a second valve body 7, a liquid passage portion 12, and a coupling member 13 which are integrally formed of an elastic material.

The valve assembly 11 (the first valve body 6 and the second valve body 7) is not limited to any particular material, but should preferably be a material having appropriate elasticity and restorability, e.g., any of various rubber materials such as silicone rubber or the like or any of various thermoplastic resins such as polybutadiene, EVA, styrene-based elastomer, or the like.

As shown in FIG. 4, the liquid passage portion 12 has a polyhedral outer profile with the liquid passage space (bore) 121 defined therein. The liquid passage space 121 is of a shape for preventing a liquid from being trapped as much as possible when the liquid flows therein. Stated otherwise, the liquid passage space 121 is of a shape which does not have any portions such as a bay where the liquid tends to be trapped.

The first valve body 6 comprises a substantially cylindrical (disk-shaped) head 61 having a central line parallel to the Y-axis direction and a low height, and a neck 62 interconnecting the head 61 and the liquid passage portion 12. The neck 62 is thinner than the head 61. In the illustrated arrangement, the neck 62 has a central line slightly inclined to the Y-axis direction.

The first valve body 6 has a slit (incision) 63 defined therein which extends from a top surface 611 of the head 61 through the neck 62 to the liquid passage space 121. The slit 63 lies parallel to the X-axis direction on the top surface 611.

As shown in FIG. 5, the second valve body 7 comprises a substantially cylindrical (disk-shaped) head 71 having a central line parallel to the X-axis direction and a low height, and a neck 72 interconnecting the head 71 and the liquid passage portion 12. The neck 72 is thinner than the head 71.

The second valve body 7 has a slit (incision) 73 defined therein which extends from a top surface 711 of the head 71 through the neck 72 to the liquid passage space 121. The slit 73 lies parallel to the Y-axis direction on the top surface 711. A straight portion which defines a part of the liquid passage space 121 connects an end of the slit 63 of the first valve body 6 and an end of the slit 73 of the second valve body 7.

The central lines of the first valve body 6 and the second valve body 7 are skew lines. Therefore, the connector 1 is advantageous in that the volume of the liquid passage space 121 is much smaller than if those central lines intersect on the same plane.

The coupling member 13 is in the form of a hollow cylinder disposed parallel to the X-axis direction and has an end coupled to the liquid passage portion 12. The coupling member 13 has an interior space communicating with the liquid passage space 121.

As shown in FIG. 2, the valve assembly 11 is coupled and fixed to the tubular member 5 with the other end of the tubular member 5 inserted in the coupling member 13. With this arrangement, the flow passage 51 in the male joint member 50 communicates with the liquid passage space 121.

Figure 6:
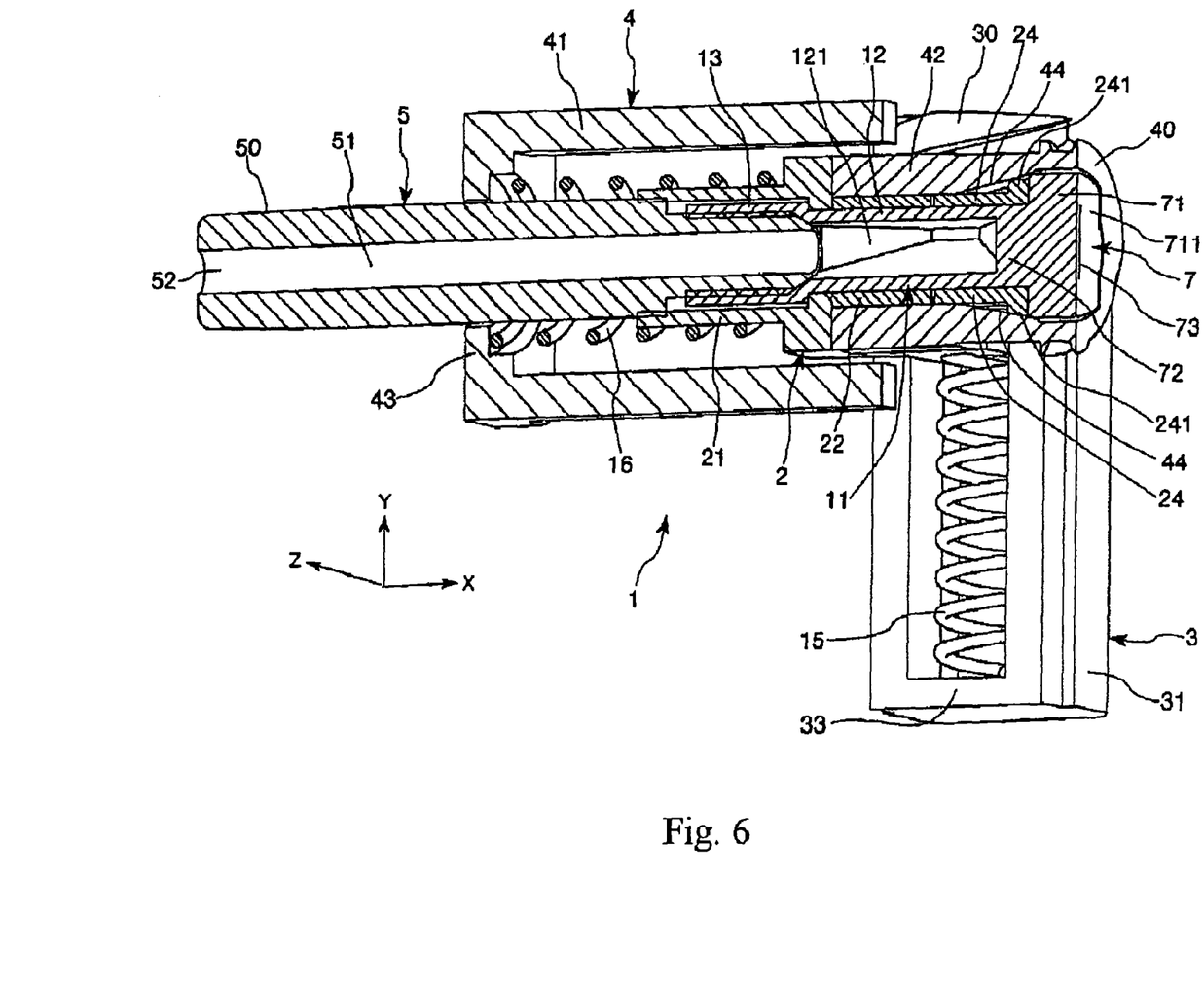
FIG. 6 is a sectional perspective view of the connector shown in FIG. 1.

The valve assembly 11 as described above is supported on and fixed to the support body 2. The support body 2 has a hollow cylindrical member 21 positioned concentrically around the coupling member 13, and a case 22 accommodating a portion of the liquid passage portion 12 therein. The hollow cylindrical member 21 is coupled and fixed to the tubular member 5, and the case 22 is formed contiguously to the hollow cylindrical member 21. The case 22 is inserted in the reduced-diameter member 42 of the second housing 4, and is slidable against the reduced-diameter member 42 in the X-axis direction. As shown in FIG. 6, the case 22 is held against the bottom and top surfaces of the liquid passage portion 12 and holds the liquid passage portion 12.

As shown in FIG. 2, the second housing 4 is disposed slidably against the support body 2, and is movable in a direction (the X-axis direction) perpendicular to the top surface 711 of the second valve body 7. A helical spring 16 is disposed between a bottom surface 43 of the second housing 4 and the case 22 of the support body 2 as an urging means for returning the second housing 4 to an unconnected state shown in FIGS. 1 and 2 when the second housing 4 is moved in the X-axis direction. The tubular member 5 is inserted in the helical spring 16.

In the unconnected state, the head 71 of the second valve body 7 is inserted in the second female joint port 40. The inside diameter of the second female joint port 40 in a direction perpendicular to the slit 73 (the Z-axis direction) in the second female joint port 40 is slightly smaller than the outside diameter of the head 71 in its free state. In the unconnected state, therefore, the head 71 is tightened radially from the direction perpendicular to the slit 73, reliably closing the slit 73.

As shown in FIG. 6, the second housing 4 has a tapered portion 44 which is disposed behind the second female joint port 40 and has an inside diameter along the width of the slit 73 (in the Y-axis direction). The inside diameter is progressively reduced into the second female joint port 40.

The support body 2 has a plurality of bar-shaped support members 24 supporting (abutting against) the head 71 of the second valve body 7 from the neck 72. The support members 24 project from the case 22 in the X-axis direction. The support members 24 include a pair of support members 24 that are positioned across the neck 72 in the Y-axis direction. The ends of a pair of support members 24 have respective teeth 241 projecting outwardly in abutment against the tapered surface of the tapered portion 44.

As shown in FIGS. 6 and 1, the second female joint port 40 has an inside diameter along the width of the slit 73 (in the Y-axis direction), greater than the inside diameter thereof in a direction perpendicular to the width of the slit 73 (the Z-axis direction). Consequently, when a male lure 200 is inserted into the second female joint port 40, the male lure 200 is fitted in the portion thereof whose inside diameter is smaller in the Z-axis direction and is not pinched by the tapered portion 44. The male lure 200 can thus smoothly be inserted into the second female joint port 40.

Figure 7:
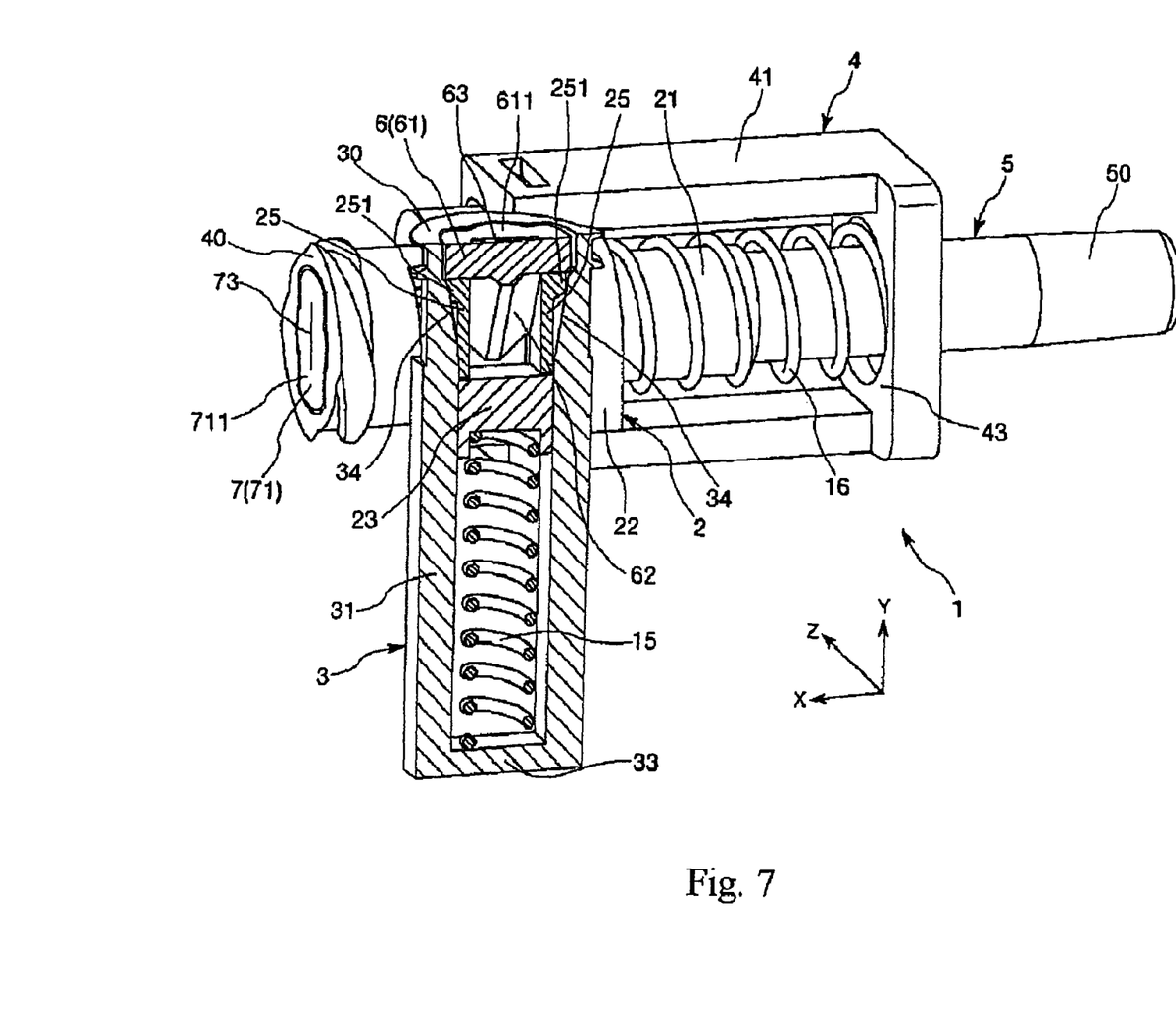
FIG. 7 is a sectional perspective view of the connector shown in FIG. 1.

As shown in FIG. 7, the support body 2 has a spring seat 23 inserted in the housing body 31 of the first housing 3. The spring seat 23 is formed contiguously to the case 22. The spring seat 23 is slidable in the Y-axis direction in the housing body 31. Therefore, the first housing 3 is movable with respect to the support body 2 in a direction (the Y-axis direction) perpendicular to the top surface 611 of the first valve body 6.

A helical spring 15 is disposed between a bottom surface 33 of the first housing 3 and the spring seat 23 as an urging means for returning the first housing 3 to an unconnected state shown in FIG. 7 when the first housing 3 is moved in the Y-axis direction.

In the unconnected state, the head 61 of the first valve body 6 is inserted in the first female joint port 30. The inside diameter of the first female joint port 30 in a direction perpendicular to the slit 63 (the Z-axis direction) in the first female joint port 30 is slightly smaller than the outside diameter of the head 61 in its free state. In the unconnected state, therefore, the head 61 is tightened radially from the direction perpendicular to the slit 63, reliably closing the slit 63.

The first housing 3 has a tapered portion 34 which is disposed behind the first female joint port 30 and has an inside diameter along the width of the slit 63 (in the X-axis direction). The inside diameter is progressively reduced into the first female joint port 30.

The first housing 3 has a plurality of bar-shaped support members 25 supporting (abutting against) the head 61 of the first valve body 6 from the neck 62. The support members 25 project from the spring seat 23 in the Y-axis direction. The support members 25 include a pair of support members 25 that are positioned across the neck 62 in the X-axis direction. The ends of a pair of support members 25 have respective teeth 251 projecting outwardly in abutment against the tapered surface of the tapered portion 34.

As shown in FIGS. 7 and 1, the first female joint port 30 has an inside diameter along the width of the slit 63 (in the X-axis direction), greater than the inside diameter thereof in a direction perpendicular to the width of the slit 63 (the Z-axis direction). Consequently, when a male lure 100 is inserted into the first female joint port 30, the male lure 100 is fitted in the portion thereof whose inside diameter is smaller in the Z-axis direction and is not pinched by the tapered portion 34. The male lure 100 can thus smoothly be inserted into the first female joint port 30.

A state of the connector 1 when the male lure 100 such as those used in a fluid infusion set is connected to the first female joint port 30 will be described below with reference to FIGS. 8, 9, and 10.

Figure 8:
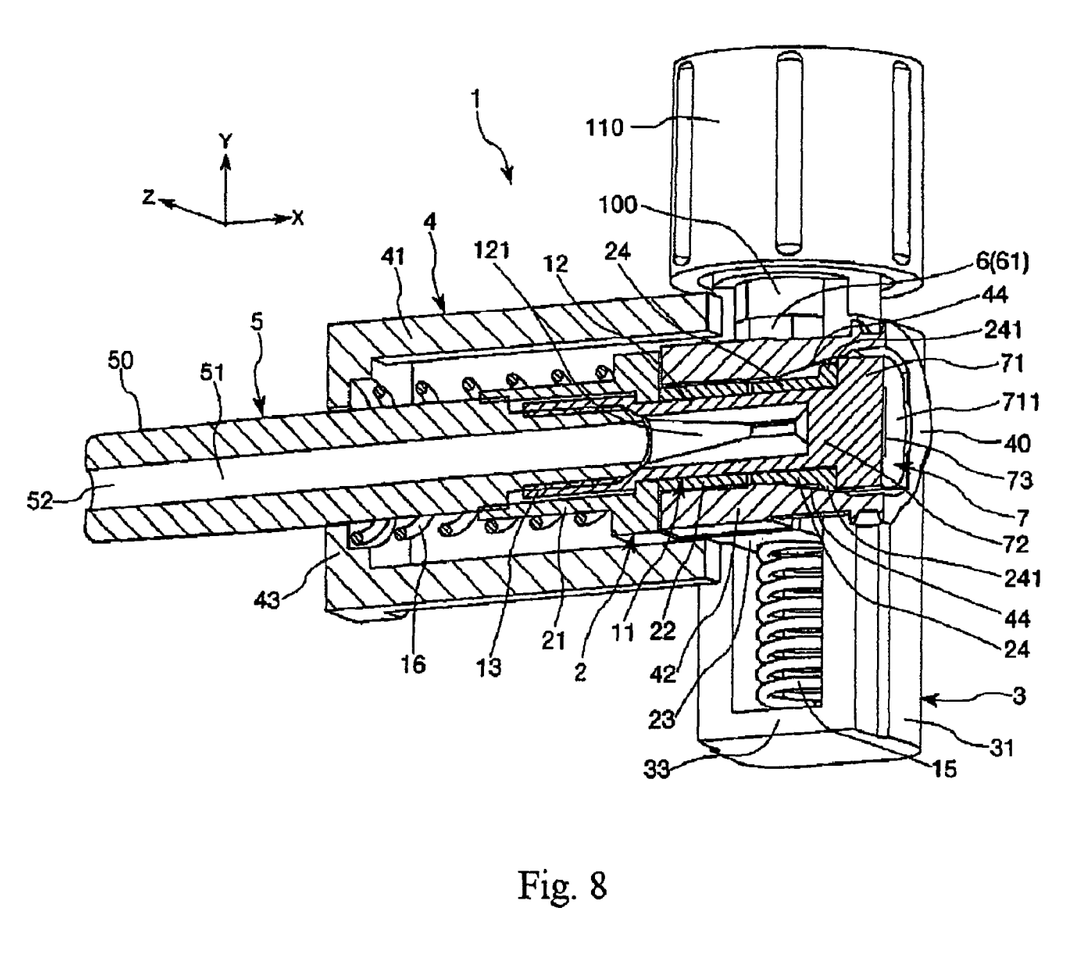
FIG. 8 is a sectional perspective view of the connector shown in FIG. 1.

As shown in FIG. 8, when the male lure 100 is inserted in and connected to the first female joint port 30, a screw lock 110 on the male lure 100 is threaded over an externally threaded outer circumferential surface of the first female joint port 30. The male lure 100 can thus reliably be secured in position.

Figure 9:
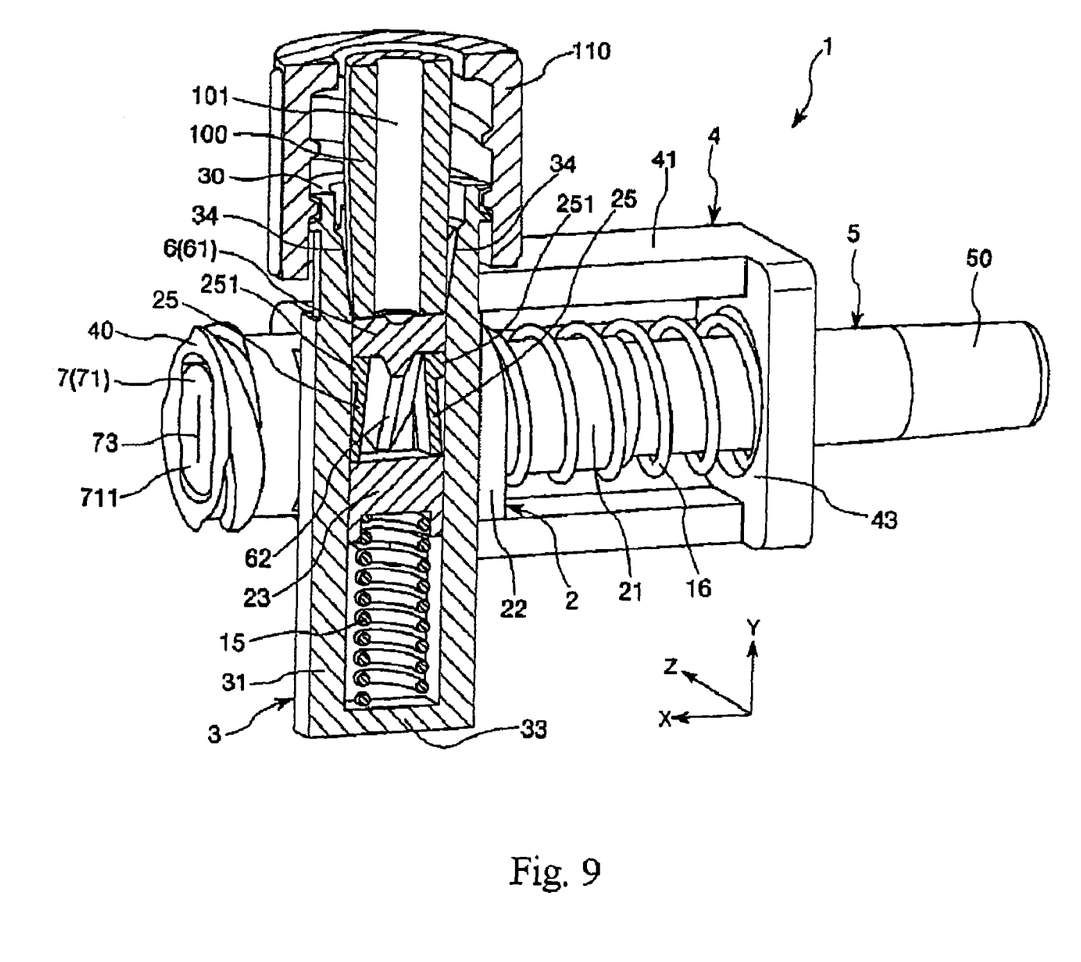
FIG. 9 is a sectional perspective view of the connector shown in FIG. 1.

As shown in FIG. 9, for connecting the male lure 100 to the first female joint port 30, the first housing 3 is gripped and the tip end of the male lure 100 is inserted into the first female joint port 30. The tip end face of the male lure 100 presses the top surface 611 of the first valve body 6, compressing the helical spring 15 and moving the first housing 3, the first valve body 6 (the valve assembly 11), and the support body 2 relatively in the Y-axis direction. At this time, since the first valve body 6 passes through the tapered portion 34 and moves together with the support members 25 into the first housing 3, the neck 62 is pressed and deformed along the width of the slit 63 (in the X-axis direction) indirectly through the support members 25 by the tapered surface of the tapered portion 34, and the head 61 is pressed and deformed in the same direction directly by the tapered surface of the tapered portion 34. As shown in FIG. 10, therefore, the slit 63 is opened over its entire length, bringing a flow passage 101 in the male lure 100 into fluid communication with the flow passage 51 in the male joint member 50 through the slit 63 and the liquid passage space 121. As shown in FIG. 10, the male lure 100 is fitted in and secured to the inner circumferential surface in the Z-axis direction of the first female joint port 30.

When the male lure 100 is thus inserted in and connected to the first female joint port 30, as the support members 25 support the head 61, the pressing force from the male lure 100 is not transmitted to the liquid passage portion 12, which is thus prevented from being deformed. As a result, any change caused in the volume of the liquid passage space 121 before and after the male lure 100 is attached or detached is extremely small. Consequently, when the male lure 100 is connected, the liquid in the flow passage 51 is prevented from being pushed out of an opening 52 (positive flow), or conversely when the male lure 100 is removed, the liquid is prevented from being drawn from the opening 52 into the flow passage 51 (backward flow). Drawbacks caused by these flows are thus prevented.

When the first valve body 6 passes through the tapered portion 34, since the neck 62 slides against the tapered surface of the tapered portion 34 through the hard support members 25, the sliding resistance is small and the neck 62 is prevented from being worn.

Figure 10:
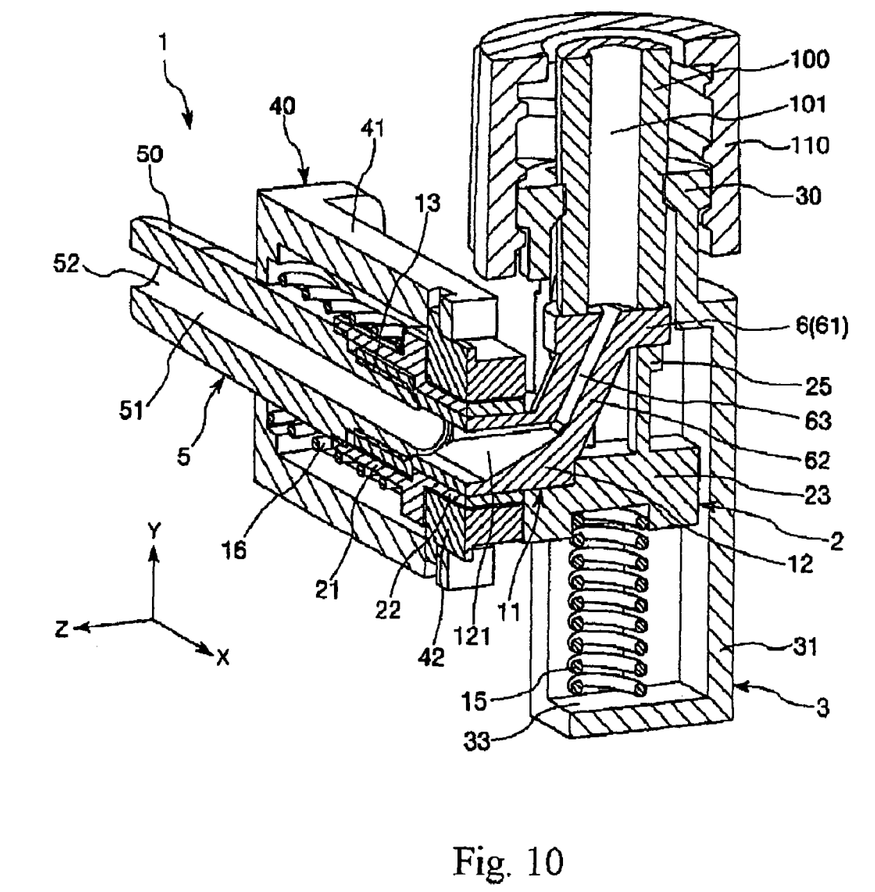
FIG. 10 is a sectional perspective view of the connector shown in FIG. 1.

In a connected state shown in FIGS. 8 through 10, when a liquid such as a medicinal solution or the like flows in from the flow passage 101 in the male lure 100, the liquid passes successively through the slit 63, the liquid passage space 121, and the flow passage 51 in the male joint member 50, and flows out of the opening 52 of the male joint member 50. At this time, as can be seen most clearly in FIG. 10, since the liquid passage space 121 is of a shape for preventing the liquid from being trapped (a shape free of bays), almost all the liquid flowing in from the flow passage 101 in the male lure 100 flows into the male joint member 50 without being trapped.

When air in the liquid passage space 121 is to replaced with a liquid such as a medicinal solution or the like, air is less likely to remain in the liquid passage space 121, and can be replaced reliably with the liquid, i.e., the connector 1 can be primed reliably.

When the male lure 100 is removed from the connected state shown in FIGS. 8 through 10, the first housing 3 is restored under the restoring force of the helical spring 15 to the position where the inner circumferential surface of the first female joint port 30 tightens the head 61 of the first valve body 6. The slit 63 is now closed, so that the connector 1 is brought back to the unconnected state shown in FIGS. 1 and 7.

A state of the connector 1 when the male lure 200 such as those used in a fluid infusion set is connected to the second female joint port 40 will be described below with reference to FIGS. 11 and 12.

Figure 11:
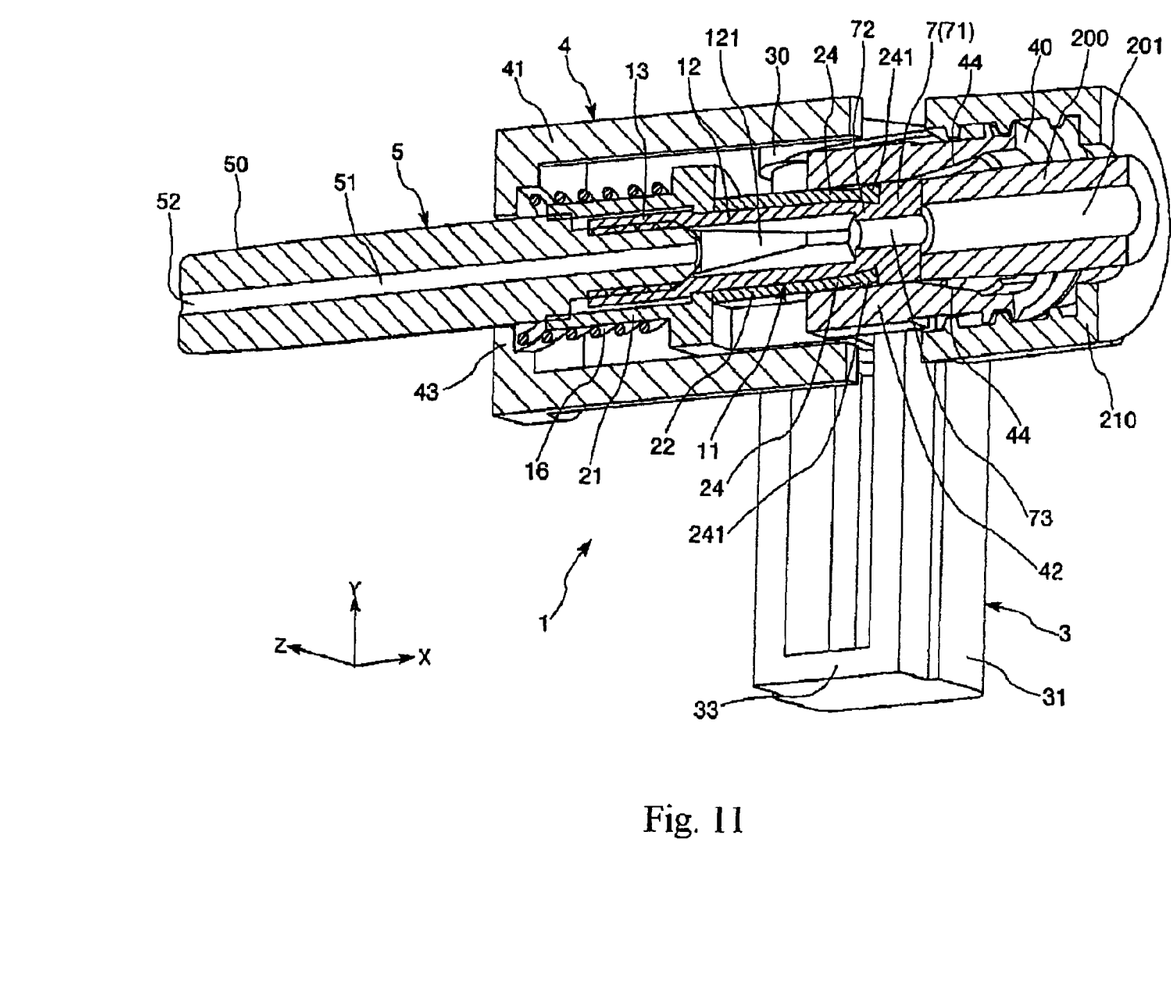
FIG. 11 is a sectional perspective view of the connector shown in FIG. 1.

As shown in FIG. 11, when the male lure 200 is inserted in and connected to the second female joint port 40, a screw lock 210 is threaded over an externally treaded outer circumferential surface of the second female joint port 40. The male lure 200 can thus reliably be fixed.

When the male lure 200 is connected to the second female joint port 40, the second housing 4 is gripped and the tip end of the male lure 200 is inserted into the second female joint port 40. The tip end face of the male lure 200 presses the top surface 711 of the second valve body 7, compressing the helical spring 16 and moving the second housing 4, the second valve body 7 (the valve assembly 11), and the support body 2 relatively in the Y-axis direction. At this time, since the second valve body 7 passes through the tapered portion 44 and moves together with the support members 24 into the second housing 4, the neck 72 is pressed and deformed in the width of the slit 73 (in the Y-axis direction) indirectly through the support members 24 by the tapered surface of the tapered portion 44, and the head 71 is pressed and deformed in the same direction directly by the tapered surface of the tapered portion 44. As shown in FIG. 12, therefore, the slit 73 is opened over its entire length, so that a flow passage 201 in the male lure 200 is brought into fluid communication with the flow passage 51 in the male joint member 50 through the slit 73 and the liquid passage space 121. As shown in FIG. 12, the male lure 200 is fitted in and secured to the inner circumferential surface in the Z-axis direction of the second female joint port 40.

When the male lure 200 is thus inserted in and connected to the second female joint port 40, as the support members 24 support the head 71, the pressing force from the male lure 200 is not transmitted to the liquid passage portion 12, which is thus prevented from being deformed. As a result, any change caused in the volume of the liquid passage space 121 before and after the male lure 200 is attached or detached is extremely small. Consequently, when the male lure 200 is connected, the liquid in the flow passage 51 is prevented from being pushed out of the opening 52 (positive flow), or conversely when the male lure 200 is removed, the liquid is prevented from being drawn from the opening 52 into the flow passage 51 (backward flow). Drawbacks caused by these flows are thus prevented.

When the second valve body 7 passes through the tapered portion 44, since the neck 72 slides against the tapered surface of the tapered portion 44 through the hard support members 24, the sliding resistance is small and the neck 72 is prevented from being worn.

Figure 12:
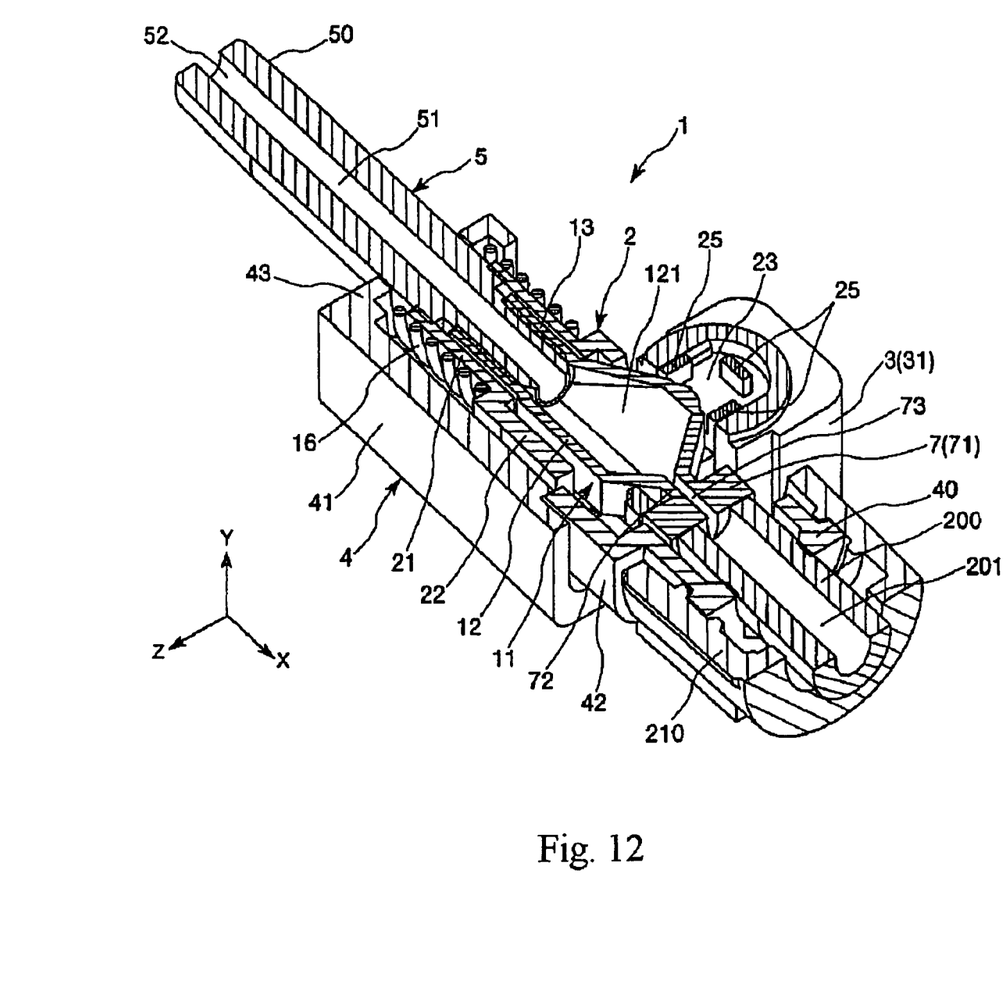
FIG. 12 is a sectional perspective view of the connector shown in FIG. 1.

In a connected state shown in FIGS. 11 and 12, when a liquid such as a medicinal solution or the like flows in from the flow passage 201 in the male lure 200, the liquid passes successively through the slit 73, the liquid passage space 121, and the flow passage 51 in the male joint member 50, and flows out of the opening 52 of the male joint member 50. At this time, as can be seen most clearly in FIG. 12, since the liquid passage space 121 is of a shape for preventing the liquid from being trapped (a shape free of bays), almost all the liquid flowing in from the flow passage 201 in the male lure 200 flows into the male joint member 50 without being trapped.

When the male lure 200 is removed from the connected state, the second housing 4 is restored under the restoring force of the helical spring 16 to the position where the inner circumferential surface of the second female joint port 40 tightens the head 71 of the second valve body 7. The slit 73 is now closed, so that the connector 1 is brought back to the unconnected state shown in FIGS. 1, 2, and 6.

In the above description, the male lures 100, 200 are connected to one of the first female joint port 30 and the second female joint port 40. However, the connector 1 may be used by connecting the male lures 100, 200 simultaneously to the first female joint port 30 and the second female joint port 40.

With the connector 1 described above, inasmuch as the first housing 3 and the second housing 4 are movable respectively with respect to the first valve body 6 and the second valve body 7 which are fixed to the support body 2, any change caused in the volume of the liquid passage space 121 before and after the male lures 100, 200 are attached or detached is extremely small. Consequently, when the male lures 100, 200 are connected, the liquid in the flow passage 51 is prevented from being pushed out of the opening 52 (positive flow), or conversely when the male lures 100, 200 are removed, the liquid is prevented from being drawn from the opening 52 into the flow passage 51 (backward flow). Drawbacks caused by these flows are thus prevented.

According to the present invention, the liquid passage portion 12, the first valve body 6, and the second valve body 7 should preferably be integrally formed as with the embodiment, though they may be separate members. The integral structure makes it possible to provide the liquid passage space 121 with a smooth inner wall for more reliably preventing the liquid from being trapped therein and easily making the connector liquid-tight.

The urging means for urging the first valve body 6 and the second valve body 7 are not limited to the helical springs 15, 16, but may be other springs. The material of the urging means is not limited to a metal material such as stainless steel or the like, but may be a rubber material such as silicone rubber or the like.

The material of the support body 2, the first housing 3, the second housing 4, and the tubular member 5 (the male joint member 50) is not limited to any particular materials, but should preferably be a material having suitable hardness, e.g., any of various polymer materials such as polyethylene, polypropylene, polycarbonate, or the like.

In the present embodiment, the connector has two female joint ports. However, the connector according to the present invention may have one female joint port or three or more female joint ports.

Although the connector according to the present invention has been described above with respect to the illustrated embodiment, the connector is not limited to the illustrated embodiment, but the various parts of the connector may be replaced with parts of any desired structures which are capable of performing the same functions. Furthermore, any desired structures may be added to the connector.

INDUSTRIAL APPLICABILITY

With the connector according to the present invention, as the flow passage is reliably opened and closed when the tube is connected and disconnected, the flow passage is prevented from being contaminated. The liquid is prevented from being trapped in the connector. Therefore, the connector according to the present invention has industrial applicability.

The invention claimed is:

1. A connector comprising:
a tubular male joint member;
a liquid passage portion having a liquid passage space defined therein in fluid communication with an interior of said male joint member, said liquid passage space being of a shape preventing liquid from being trapped therein when the liquid flows in said liquid passage space;
a first female joint port and a second female joint port which are capable of receiving a tube;
a first valve body having a head and a neck interconnecting said head and said liquid passage portion, said neck being thinner than said head, said first valve body having a slit extending from a top surface of said head to said liquid passage space, said first valve body being made of an elastic material;
a second valve body having a head and a neck interconnecting said head and said liquid passage portion, said neck being thinner than said head, said second valve body having a slit extending from a top surface of said head to said liquid passage space, said second valve body being made of an elastic material;
a straight portion which defines a part of said liquid passage space and connects an end of said slit of said first valve body and an end of said slit of said second valve body;
wherein when a tube is connected to said first female joint port, said first valve body is deformed to open the slit of said first valve body to bring an interior of the tube and an interior of said male joint member into fluid communication with each other through the slit of said first valve body and said liquid passage space; and
when a tube is connected to said second female joint port, said second valve body is deformed to open the slit of said second valve body to bring an interior of the tube and the interior of said male joint member into fluid communication with each other through the slit of said second valve body and said liquid passage space.

2. A connector according to claim 1, wherein said first female joint port or said second female joint port and said male joint member have respective central lines extending substantially parallel to each other.

3. A connector according to claim 1, wherein said liquid passage portion, said first valve body, and said second valve body are integrally formed with each other.

4. A connector according to claim 1, wherein at least one of said first female joint port and said second female joint port is movable in the direction of a central line thereof relatively to the corresponding valve body.

5. A connector comprising:
a tubular male joint member;
a liquid passage portion having a liquid passage space defined therein in fluid communication with an interior of said male joint member;
a first female joint port and a second female joint port which are capable of receiving a tube;
a first valve body disposed in said first female joint port and made of an elastic material, said first valve body having a slit;
a second valve body disposed in said second female joint port and made of an elastic material, said second valve body having a slit;
a straight portion which defines a part of said liquid passage space and connects an end of said slit of said first valve body and an end of said slit of said second valve body;
the central line of said first female joint port and the central line of said second female joint port are skew lines;
wherein when a tube is connected to said first female joint port, said first valve body is deformed to open the slit of said first valve body to bring an interior of the tube and an interior of said male joint member into fluid communication with each other through the slit of said first valve body; and
when a tube is connected to said second female joint port, said second valve body is deformed to open the slit of said second valve body to bring an interior of the tube and the interior of said male joint member into fluid communication with each other through the slit of said second valve body.

6. A connector according to claim 5, wherein said first female joint port is movable in the direction of the central line thereof relatively to said first valve body, and said second female joint port is movable in the direction of the central line thereof relatively to said second valve body.

7. A connector according to claim 2, wherein said liquid passage portion, said first valve body, and said second valve body are integrally formed with each other.

8. A connector according to claim 2, wherein at least one of said first female joint port and said second female joint port is movable in the direction of a central line thereof relatively to the corresponding valve body.

9. A connector according to claim 5, wherein said fluid passage space is of a shape for preventing a liquid from being trapped therein when the liquid flows in said liquid passage space.

10. A connector according to claim 6, wherein said fluid passage space is of a shape for preventing a liquid from being trapped therein when the liquid flows in said liquid passage space.

* * * * *